US009483792B2

(12) United States Patent
Podmore et al.

(10) Patent No.: US 9,483,792 B2
(45) Date of Patent: Nov. 1, 2016

(54) SCREEN-BASED METHOD AND SYSTEM FOR SIZING AN ORAL APPLIANCE

(71) Applicant: ApniCure, Inc., Redwood City, CA (US)

(72) Inventors: Jonathan L. Podmore, San Carlos, CA (US); Kenneth Mejia, San Francisco, CA (US)

(73) Assignee: Apnicure, Inc., Redwood City, CA (US)

( * ) Notice: Subject to any disclaimer, the term of this patent is extended or adjusted under 35 U.S.C. 154(b) by 660 days.

(21) Appl. No.: 13/787,237

(22) Filed: Mar. 6, 2013

(65) Prior Publication Data

US 2014/0088437 A1 Mar. 27, 2014

Related U.S. Application Data

(60) Provisional application No. 61/647,446, filed on May 15, 2012.

(51) Int. Cl.
| | |
|---|---|
| *G06Q 30/00* | (2012.01) |
| *G06Q 30/06* | (2012.01) |
| *A61F 5/56* | (2006.01) |
| *A61B 5/00* | (2006.01) |
| *A61B 5/107* | (2006.01) |
| *A61C 9/00* | (2006.01) |
| *A61C 5/14* | (2006.01) |

(52) U.S. Cl.
CPC ......... *G06Q 30/0641* (2013.01); *A61B 5/0088* (2013.01); *A61B 5/1079* (2013.01); *A61B 5/72* (2013.01); *A61B 5/742* (2013.01); *A61B 5/748* (2013.01); *A61C 9/004* (2013.01); *A61C 9/0006* (2013.01); *A61C 9/008* (2013.01); *A61C 9/0053* (2013.01); *A61F 5/566* (2013.01); *G06Q 30/0643* (2013.01); *A61C 5/14* (2013.01); *G06Q 30/0631* (2013.01)

(58) Field of Classification Search
CPC .................................. G06Q 30/0601–30/0645
USPC ................................................ 705/26.1–27.2
See application file for complete search history.

(56) References Cited

U.S. PATENT DOCUMENTS

| | | | |
|---|---|---|---|
| 2,219,559 | A | 10/1940 | Lentz |
| 3,132,647 | A | 5/1964 | Corniello |
| 3,898,736 | A | 8/1975 | Bergersen |
| 4,169,473 | A | 10/1979 | Samelson |
| 4,304,227 | A | 12/1981 | Samelson |
| 4,669,459 | A | 6/1987 | Spiewak et al. |
| 4,676,240 | A | 6/1987 | Gardy |

(Continued)

FOREIGN PATENT DOCUMENTS

| | | |
|---|---|---|
| WO | WO-2008083857 A1 | 7/2008 |

OTHER PUBLICATIONS

Molinari, G. E. (Oct. 2006). September is a good time to keep smiling. Michigan Chronicle Retrieved from http://search.proquest.com/docview/390123617?accountid=14753.*

(Continued)

*Primary Examiner* — Resha Desai
(74) *Attorney, Agent, or Firm* — Wilson Sonsini Goodrich & Rosati (57) ABSTRACT

An oral appliance is sized by obtaining a scaled image of a patient's dental arch. Dimensions of the arch are marked on a screen image, and the processor chooses an oral appliance having a best fit for a particular patient.

10 Claims, 7 Drawing Sheets

(56) References Cited

U.S. PATENT DOCUMENTS

| | | | |
|---|---|---|---|
| 4,997,368 A | 3/1991 | Mayer et al. | |
| 5,385,155 A * | 1/1995 | Kittelsen | A61C 5/00 128/859 |
| 5,465,734 A | 11/1995 | Alvarez et al. | |
| 5,915,385 A | 6/1999 | Hakimi | |
| 5,957,133 A | 9/1999 | Hart | |
| 6,089,868 A | 7/2000 | Jordan et al. | |
| 6,467,484 B1 | 10/2002 | De Voss | |
| 6,494,209 B2 | 12/2002 | Kulick | |
| 6,736,637 B2 | 5/2004 | Bond | |
| 6,877,513 B2 | 4/2005 | Scarberry et al. | |
| 6,955,172 B2 | 10/2005 | Nelson et al. | |
| 6,976,491 B2 | 12/2005 | D'Agosto | |
| 7,073,505 B2 | 7/2006 | Nelson et al. | |
| 7,073,506 B2 | 7/2006 | Robertson et al. | |
| 7,182,082 B2 | 2/2007 | Hoffrichter | |
| 7,328,698 B2 | 2/2008 | Scarberry et al. | |
| 8,122,889 B2 | 2/2012 | Vaska et al. | |
| 8,402,973 B2 | 3/2013 | Podmore et al. | |
| 2001/0023413 A1 * | 9/2001 | Fukuma | G06Q 30/06 351/159.19 |
| 2003/0138752 A1 | 7/2003 | Bergersen | |
| 2005/0166928 A1 | 8/2005 | Jiang | |
| 2005/0166929 A1 | 8/2005 | Jiang | |
| 2005/0236003 A1 | 10/2005 | Meader | |
| 2006/0096600 A1 | 5/2006 | Witt et al. | |
| 2006/0282010 A1 | 12/2006 | Martin et al. | |
| 2007/0254247 A1 | 11/2007 | Yamamoto et al. | |
| 2007/0277818 A1 | 12/2007 | Chen | |
| 2008/0071559 A1 * | 3/2008 | Arrasvuori | G06Q 30/06 705/26.1 |
| 2008/0188947 A1 | 8/2008 | Sanders | |
| 2008/0210244 A1 | 9/2008 | Keropian | |
| 2008/0216843 A1 | 9/2008 | Jiang | |
| 2008/0221697 A1 | 9/2008 | Graser | |
| 2009/0120446 A1 | 5/2009 | Vaska et al. | |
| 2009/0120447 A1 | 5/2009 | Vaska et al. | |
| 2009/0123886 A1 | 5/2009 | Vaska | |
| 2010/0037166 A1 | 2/2010 | Chandrasekar et al. | |
| 2010/0159414 A1 * | 6/2010 | Crucs | A61B 6/14 433/68 |
| 2011/0195373 A1 | 8/2011 | Waugh | |
| 2012/0037166 A1 | 2/2012 | Podmore et al. | |
| 2013/0130872 A1 | 5/2013 | Benne et al. | |

OTHER PUBLICATIONS

International search report and written opinion dated Sep. 23, 2013 for PCT/US2013/040152.

Cartwright et al., "The effects of a non-surgical treatment for obstructive sleep apnea: the tongue retaining device;" JAMA, Aug. 1982; 248(6): 705-709.

Hoffstein, "Review of oral appliances for treatment of sleep-disordered breathing," Sleep Breath, 2007 Mani 1(1):1-22.

International search report and written opinion dated Nov. 22, 2011 for PCT/US2011/043574.

Notice of allowance dated Feb. 1, 2013 for U.S. Appl. No. 12/857,375.

Office action dated Oct. 15, 2012 for U.S. Appl. No. 12/857,375.

* cited by examiner

SCREEN-BASED METHOD AND SYSTEM FOR SIZING AN ORAL APPLIANCE

CROSS-REFERENCE TO RELATED APPLICATIONS

This application claims the benefit of provisional patent application 61/647,446, filed on May 15, 2012, the full disclosure of which is incorporated herein by reference.

BACKGROUND OF THE INVENTION

Field of the Invention

The present invention relates generally to medical devices and methods. In particular, the present invention relates to a method and a system for sizing an oral device to allow selection of a particular device having a proper fit for an individual patient from an inventory of such devices.

Mouthpieces, mouth guards, and a variety of other oral devices are worn by patients for a variety of purposes. Of particular interest to the present invention, certain oral devices and appliances can be used for treating obstructive sleep apnea (OSA) which is a serious medical condition resulting from temporary airway blockage which occurs as a patient sleeps. A variety of devices have been developed over the years for altering pressure, tongue position, and other characteristics of the oral cavity in order to minimize the occurrence of sleep apnea in patients. One such oral appliance is described in U.S. Pat. No. 8,122,889, assigned to the assignee of the present application, the full disclosure of which is incorporated herein by reference.

Many oral appliances are fitted individually to the patient being treated, typically by taking a full dental impression, forming molds from the impression, and preparing devices which closely conform to the patient's dentition and jaws in order to fit the patient with great accuracy. While such highly accurate fittings may in some cases optimize patient comfort, in all cases they will take time, are inconvenient for the patient, and significantly increase the cost of the oral device.

Thus, for a wide class of oral devices, it will be desirable to provide methods and systems for fitting particular devices from inventories of pre-manufactured devices having different sizes and geometries to individual patients. In some cases, such as with athletic and other mouth guards, the fitting can be rather crude. As described, for example, in U.S. Pat. No. 5,385,155, in some instances it is necessary only to provide devices in three sizes (small, medium, and large) where the devices can be selected using a single sizing template 40 which can be compared to a dental impression plate 44 to determine which of the three sizes best fits the patient.

For more complex devices, such as those intended to treat sleep apnea, more accurate sizing means are desirable, and the ability to rapidly choose from a larger inventory of pre-made devices will be of great benefit. In particular, a system using multiple templates for sizing oral appliances is described in commonly owned U.S. Patent Publication 2012/0037166, the full disclosure of which is incorporated herein by reference. The systems include both a width measuring template for determining the distance between opposed molars and a least one separate arch sizing tool for determining the size and shape of the patient's dental arch. Based on this information, individual appliances can be selected from an inventory of such appliances, where the selected appliance would best fit the patient. Commonly owned co-pending application Ser. No. 13/476,655, describes another manual system which uses right and left overlays for sizing oral appliances.

While a great improvement over earlier systems, the sequential use of multiple templates requires multiple steps which can lead to inaccurate measurements. The simultaneous use of right and left overlays addresses some of the concerns with the use of sequential templates but the need to carefully manipulate the overlays can lead to errors particularly when deployed by less dexterous individuals.

Thus, it would be desirable to provide improved methods and systems for sizing oral appliances which minimize the number of steps and/or templates or overlays required, which are intuitive to use, and which are very accurate. At least some of these objectives will be met by the inventions described hereinafter.

Description of the Background Art

U.S. Pat. No. 5,385,155; U.S. Publication No. 2012/0037166; and commonly owned co-pending application Ser. No. 13/476,655 have been discussed above. U.S. Patent Publ. No. 2009/0120446 describes oral appliances for treating OSA of the type which can be usefully sized by the methods and systems of the present invention.

SUMMARY OF THE INVENTION

The present invention provides methods and devices for sizing oral appliances for an individual patient. In particular, the methods, devices, and systems of the present invention allow an oral appliance size to be selected from a plurality or "inventory" of such sizes. The methods rely on obtaining a "scaled" image of the patient's dental arch and marking specific anatomic locations on the image. By "scaled" is meant that the distances apparent on the image will be registered with the actual anatomic dimensions of the patient's dental arch. The scaling information, typically in the form of a ratio between the apparent dimensions of the image and the actual anatomic dimensions of the patient's dental arch, may be provided with the image. For example if the image is obtained with a camera or other optical scanning device, a scaling ratio may be determined by matching a size registration symbol on the image with a scaling symbol on a display of the image. Once the scaled image is obtained, the user marks specific anatomic locations on the displayed image of the dental arch, and a program or "application" selects an optimum oral appliance size based on such marked locations on the scaled image. In specific embodiments, the sizing methods can be performed using a conventional hand-held device, such as a smart phone or tablet, having an on-board camera. The camera is used to acquire the image of the dental arch, either indirectly from a wax bite or directly from the patient, and the program accessed via the device is used to scale the image and make the size selection.

In a first specific aspect of the present invention, a method for selecting an oral appliance from an inventory of oral appliances comprises presenting a scaled image of a patient's dental arch on a display. Locations on opposite sides of the dental arch (opposed locations) are marked on the image, typically between at least two of the patient's adjacent molars, usually between the first and second molars, on each side of the image. A location on the patient's incisors is then marked to obtain a length dimension measured axially between the molar locations to the incisor location. The width dimension and the length dimension are then processed by a processor which selects an oral appliance size which will accommodate the patient's dental arch based on the width and length dimensions.

In exemplary embodiments, the scaled image is obtained from a bite plate. In particular, the bite plate, such as a wax bite plate, will have a size registration symbol and will be scanned by a camera to obtain a digital image. The digital image of the bite plate is then shown on the display where the user matches the size registration symbol apparent on the image of the wax bite plate with a scaling symbol generated by the processor on the display. By increasing or reducing the size of the scaling symbol so that it will match the apparent size of the registration symbol, the processor can determine the ratio of the image dimensions to the anatomic dimensions to determine the actual dimensions of the patient's dental arch.

Alternatively, a scaled image may be obtained directly from the patient's dental arch. For example, a pressure-sensitive bite plate can be used which directly generates a dimensionally scaled electronic image of the teeth when the patient bites down on the plate. Further alternatively, an intra-oral camera may be utilized to obtain the scaled image of the dental arch. Available intra-oral imaging cameras can take images which are scaled to the anatomic dimensions. In further specific embodiments, the display may comprise a touch screen, for example a touch screen on a hand-held device, and marking may comprise touching the anatomic location as it appears on the touch screen to fix that location for the processor. Alternatively, marking may comprise aligning a cursor on a conventional computer screen with a location on the display of the conventional computer. In most instances, the processor will select the oral appliance size using the scaled dimensions, such as the scaled width and length dimensions, using a look-up table which provides the optimum oral appliance size based on the scaled anatomic dimensions.

In still other specific embodiments, the marked imaged locations and selected oral appliance size may be stored in an on-board memory in the display device. Alternatively or additionally, such image, marked locations and the selected oral appliance size may be stored in memory remote from the device. E.g. in the "cloud," or in a central location intended specifically for storing such information.

In a second specific aspect of the present invention, a device for selecting an oral appliance from an inventory of oral appliances comprises a display, a user interface, and a processor. The display will be any conventional electronic display, typically being a touch-screen display in which case the display will also provide the user interface. In other instances, the display may be configured with a keyboard or other external interface, such as in a table-top or laptop computer.

The processor is programmed to present a scaled image of the patient's dental arch to a user on the display. The processor can detect markings on the image of at least two opposed locations on the patient's molars to obtain a width dimension. The processor can also detect a marking on the image of the patient's incisors to obtain a length dimension. Based on the width and length dimensions, the processor can select an oral appliance size which will optimally accommodate the patient's oral arch, and the selected appliance size and/or a device designation, will be shown on the display.

In exemplary embodiments, the device includes both a touch-screen and an on-board camera. The camera is used for acquiring an image of the patient's dental arch, and the processor is further programmed to allow the user to scale the image by matching a scaling symbol generated by the processor and visible on the display screen with a size registration symbol on the image.

In still further specific embodiments, the device having the on-board camera and the scaling symbol on the display may be combined with a wax bite plate having the size registration symbol visible on the surface thereof. In this way, the camera device will acquire an image of the size registration symbol at the same time the image of the dental arch is acquired. When the image of the wax bite plate is displayed on the device display, the user can match the processor-generated scaling symbol with the apparent size of the registration symbol on the image, allowing the processor to determine the size ratio of the apparent image with the actual anatomic inventions. In specific embodiments, the size registration symbol may be a triangle and the user may increase and decrease the size of a triangular scaling symbol on the display screen until the triangular sizes match.

In other system embodiments, when the display device does not include an on-board camera, the system may comprise a separate intraoral camera configured to acquire a scaled image of the patient's dental arch and deliver said image to said display device and processor. Alternatively, the system may utilize a pressure-sensitive bite plate configured to generate an electronic scaled image of the patient's oral arch when the patient bites down on the plate.

DETAILED DESCRIPTION OF THE INVENTION

Figure 1:
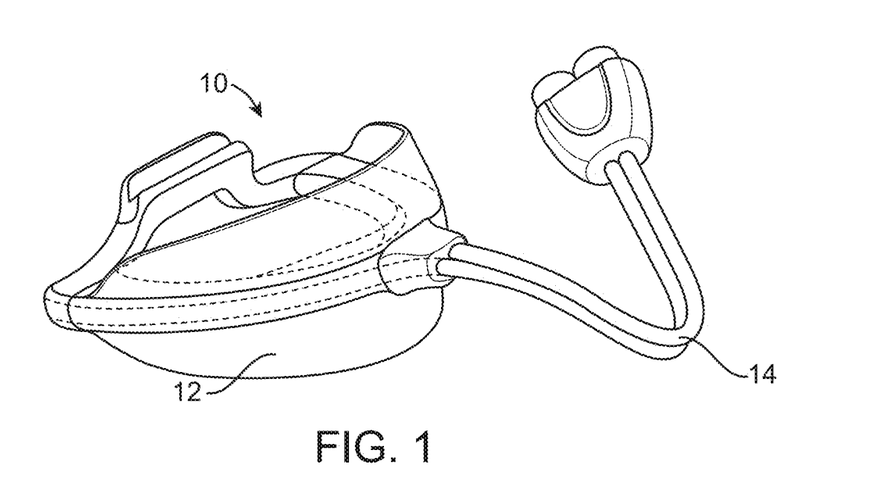
FIG. 1 illustrates an oral appliance of the type which may be sized by the methods, devices, and systems of the present invention.

An oral appliance 10 designed to treat obstructive sleep apnea (OSA) is illustrated in FIG. 1. A mouthpiece 12 provides an interface between the patient and a vacuum source via vacuum line 14. The mouthpiece will come in a plurality of sizes. For example the mouthpiece may consist of two sized components which, through different combinations, can make from six to 30 differently sized mouthpieces, often being ten differently sized mouthpieces. The present invention provides a very convenient and accurate method for selecting a mouthpiece size (from the available plurality of sizes) that will best fit an individual patient.

Selecting the proper mouthpiece size is based on the patient's dental anatomy. In particular, an image of the dental arch is obtained by any one of several techniques, and the image is uploaded to a processor which is programmed to measure the dental arch and determine the appliance size based on those measurements. In an exemplary embodiment, the program is provided in an application which can be uploaded to a hand-held device, such as a smart phone or a tablet, having an on-board camera that can be used to obtain the image, typically from a wax bite plate. A touch screen on the hand-held device can then be used to scale the image and mark key anatomic locations on the image. With that information, the application can select the best fit appliance size for the patient.

While the hand-held device with a touch screen is convenient and will often be used, the present invention can also use laptop and other computers with touch screens and without touch screen where, in the latter case, the dental arch image may be scaled and marked using a cursor. Moreover, the dental arch image can be obtained by other means, such as using an intra-oral or other camera to capture the image or using a pressure-sensitive bite plate to electronically (non-optically) capture the image.

Figure 2:
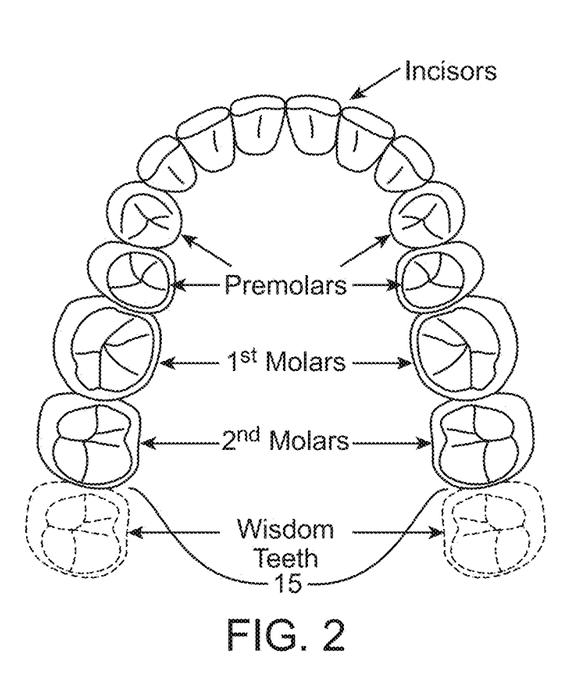
FIG. 2 illustrates a dental arch showing the locations of the molars and incisors.

The mouthpiece sizing program or application uses two dimensions taken from the image of the patient's dental arch. Referring to FIG. 2, a width dimension between the molars of the teeth is determined. This width dimension is preferably measured across gaps 15 between the first and second molars on each side of the jaw. If present, wisdom teeth are ignored for this measurement. Next, the axial length from the front edge of the incisors (front teeth) to the first and second molar gap is measured. With these two dimensions, the sizing program or application will select the patient's proper mouthpiece, usually from a look up table.

For optimum performance, the hand-held device should allow for scaling of an image and should include a camera to acquire an image. The following specific instructions are provided for the Apple iPhone® 4 and 4s and the Apple iTouch®, but it will be appreciated that other smart phones and tablets could also be used.

Figure 3:
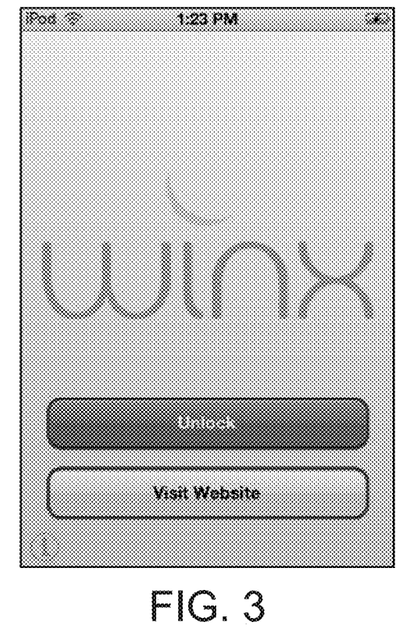
FIGS. 3-16 are screenshots illustrating use of a touch-screen display on a smart phone for performing the methods of the present invention.
Figure 4:
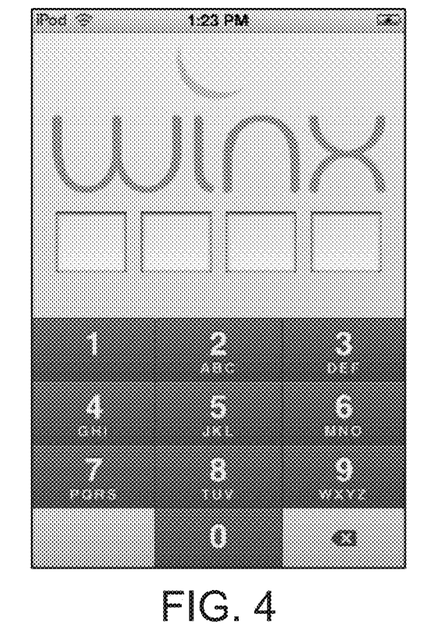
Figure 5:
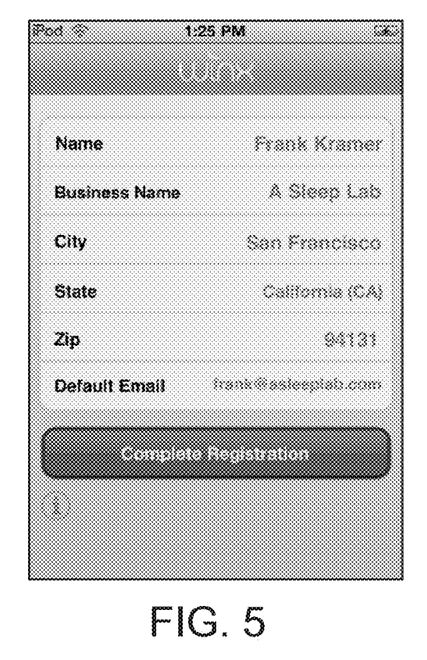

Referring to FIG. 3, a sizing program (referred to as WINX, a trademark of ApniCure, Inc., assignee of the present invention) is uploaded to the smart phone in a conventional manner. After unlocking the application (FIG. 4), a registration screen appears (FIG. 5). Contact information for the sleep professional is input on the registration screen. This information is used to verify that the program or application is being used by a sleep professional and to send a printable form of the sizing information for a given patient to the sleep professional so that the form can be filed with the patient's records.

When ready to size the oral device or mouthpiece, a home screen (FIG. 6) appears. From the home screen, the sleep professional can size the oral device. Additionally, the professional can view the sizing history of the device or patient, locate on-screen help, learn about the details of the sizing and treatment systems, view a user guide and associated troubleshooting literature, and view and/or modify program and application settings.

Figure 6:
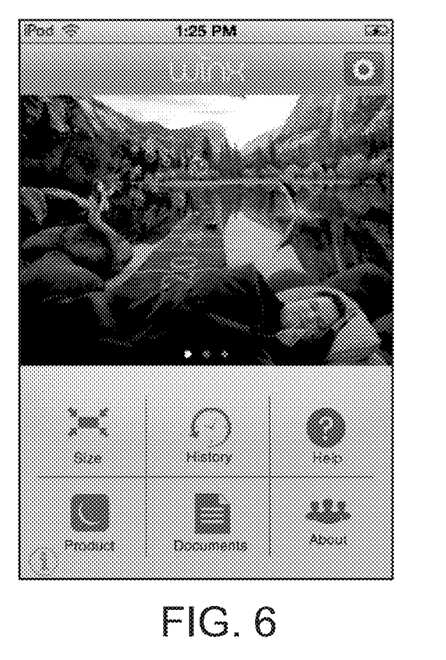
Figure 7:
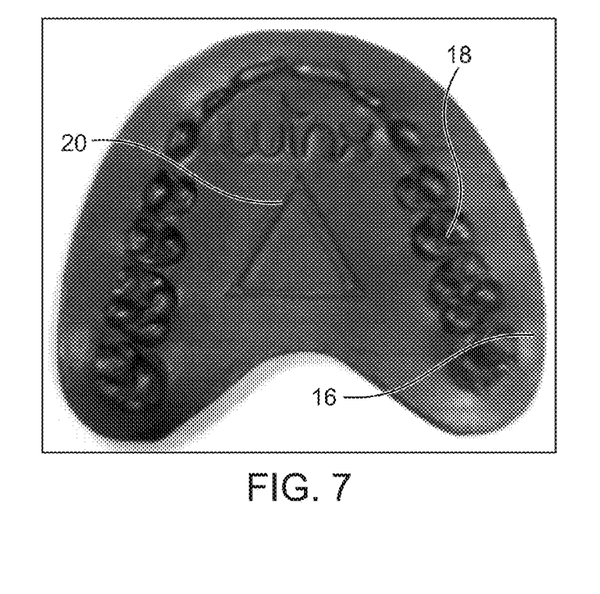
Figure 8:
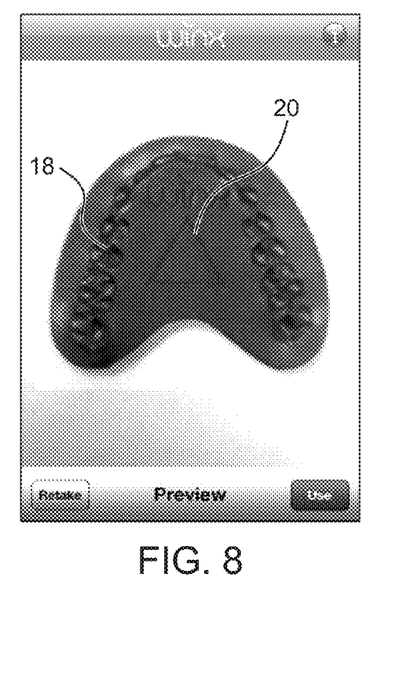

The hand-held device uses the internal camera to acquire and input an image of a patient's dental arch (bite registration) from a wax bite plate (FIG. 7). The wax bite plate is obtained in a conventional manner with the patient biting into the plate to leave visible impressions of the upper and lower dentition (teeth). The sizing process is initiated by pressing a size button on the home screen (FIG. 6). This activates the hand-held device's camera. The patient's wax bite plate should be placed on a flat, level surface. The hand-held should be held parallel to the bite plate, and at least the impression of the dentition (dental arch) and the size registration symbol (triangle 18) should be within the device screen to ensure that all necessary information is captured (FIG. 8). Once the image is properly aligned, the user presses the camera button on the bottom of the screen to capture the image.

Figure 9:
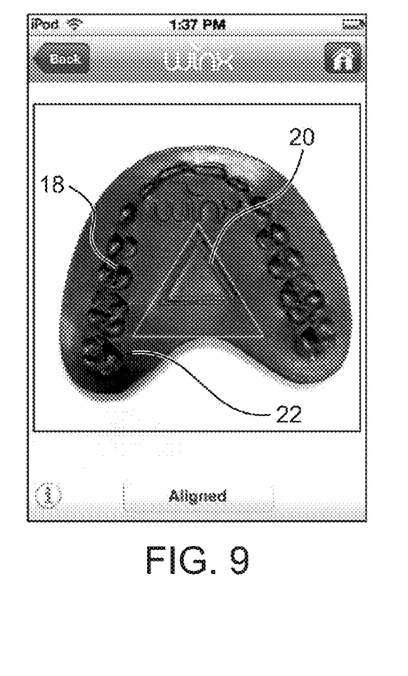
Figure 10:
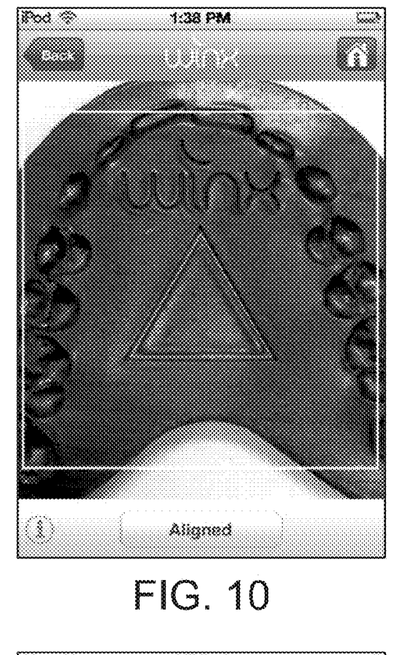

Next, the captured image needs to be scaled properly. The wax bite plate contains an equilateral triangle 18 stamped on its surface (FIGS. 7-9). After accepting the picture for use, the program presents a white, wireframe equilateral triangle 22 on the screen (FIG. 9). For Apple devices, the common finger swipe techniques can be used zoom (two finger pinch), translate (one finger swipe), and rotate (two finger turn), to align the wireframe triangle 22 with the stamped triangle 20 on the bite plate. For accurate results, the wireframe triangle 22 should rest fully inside the stamped triangle 20 (FIG. 10). "Aligned" is pressed when the triangle is properly located.

Figure 11:
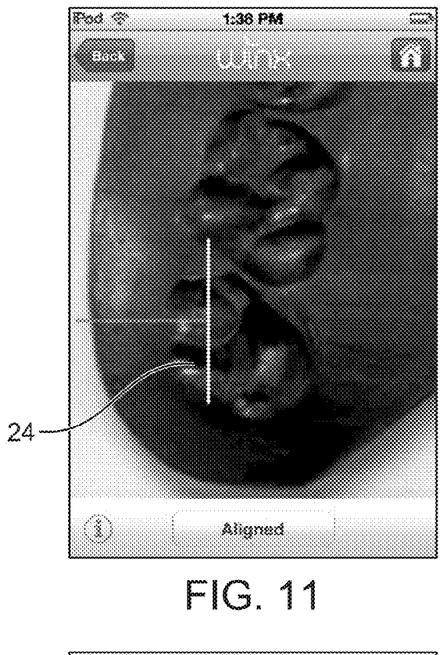
Figure 12:
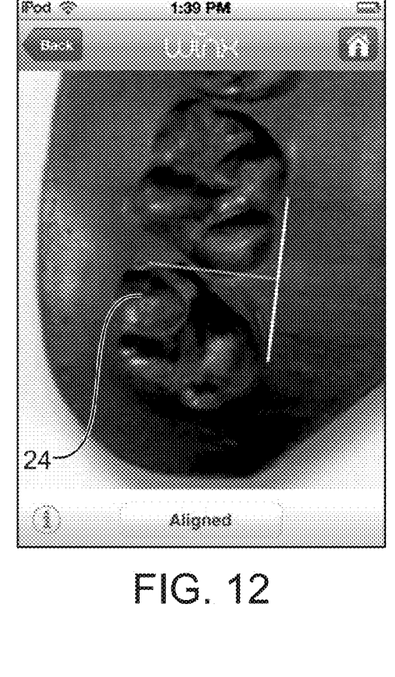
Figure 13:
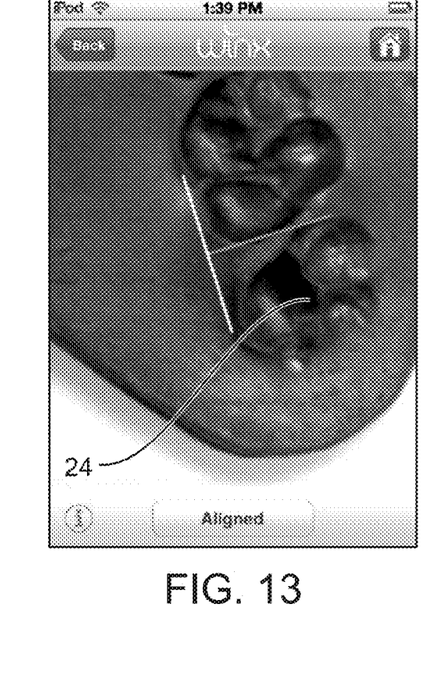

Next, the program or application asks the user to identify the locations of the first and second molar gap on both sides of the dental arch 18. A "T" 24 appears on the mobile device screen (FIG. 11). A longer portion of the "T" should rest along an inner edge of the molars. A shorter leg of the "T" should rest at the gap between the first and second molars (FIG. 12). The "T" 24 can be rotated and translated using common finger swipe techniques (two finger turn to rotate and one finger swipe to translate). Press "Aligned" when the "T" is properly located. The process is repeated on the right molars (FIG. 13).

Figure 14:
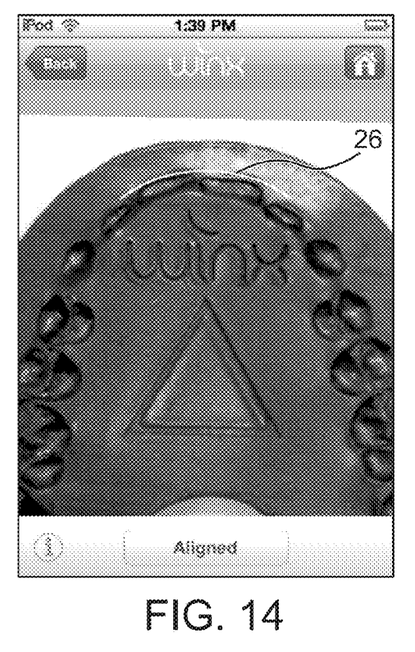

The final step of the sizing process is locating the front edge of the patient's incisors. Move an on-screen arc 26 up and down until it rests at the front edge of the incisors (FIG. 14). The arc should rest on the outermost edge of the patient's incisors. "Aligned" is pressed when the arc is properly located.

Figure 15:
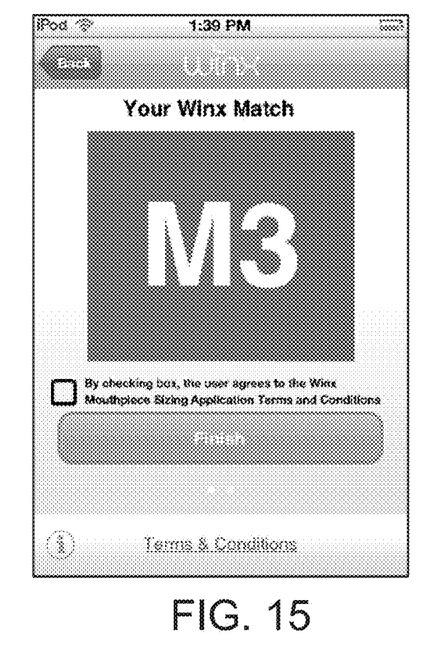
Figure 16:
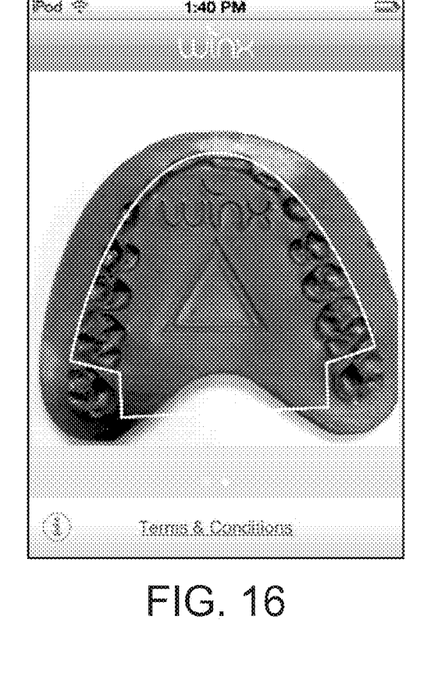

The program or application now presents a match or result screen with the properly identified mouthpiece size (FIG. 15). With a right-to-left finger swipe along the bottom edge of the screen, the patient's bite registration can be viewed with the selected mouthpiece overlaid (FIG. 16). Rotate and translate this image to verify the chosen mouthpiece fits properly on the patient's teeth. The program or application may optionally send an email with the chosen size to the email address provided during set-up and return to the home screen.

Figure 17:
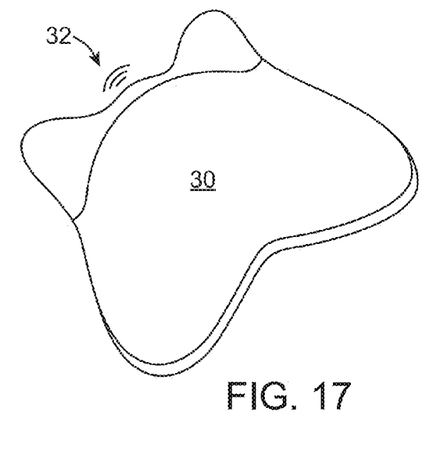
FIGS. 17 and 18 illustrate a pressure-responsive bite plate which may be used for obtaining a scaled electronic image of a patient's dental arch.
Figure 18:
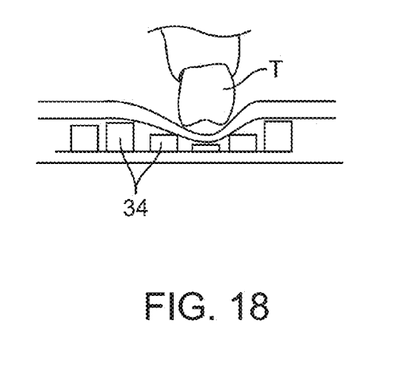

As an alternative to the use of an on-board camera as just described, a scaled image of the patient's dental arch can be obtained directly using a pressure-sensitive bite plate 32, as shown in FIG. 17. The bite plate could, for example, comprise a matrix of individual pressure-sensitive contacts 34 (FIG. 18) which, when engaged by a tooth T, would generate and electronic image of the patient's dental arch having the actual anatomic dimensions. The image information could be transmitted or otherwise sent to the display and processor either wirelessly 32 or by having a connector cable (not shown). This image would have correct anatomical dimensions and would thus be "scaled" within the requirements of the present invention.

Figure 19:
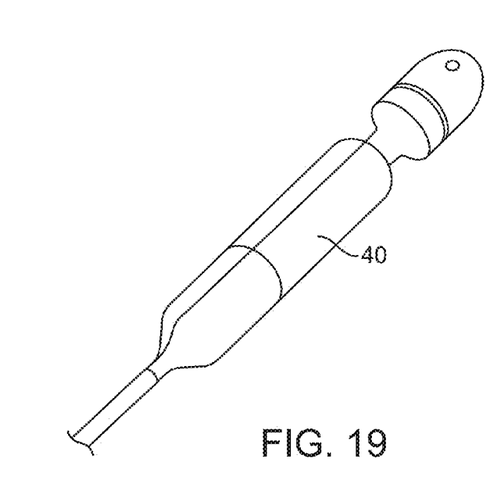
FIG. 19 illustrates an intraoral camera which may be used for obtaining a scaled image of a patient's dental arch.
Figure 20:
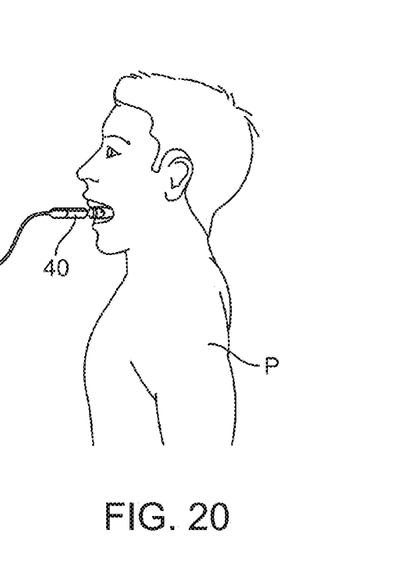
FIG. 20 illustrates use of the intraoral camera of FIG. 19.

A scaled image could also be obtained using an intra-oral camera 40 (FIG. 19) which is intended to be placed in a patient's oral cavity, as shown in FIG. 20. The camera has a wide angle or 360° angle view and can acquire the oral image which is either anatomically scaled or can be scaled using the display and processor.

Figure 21:
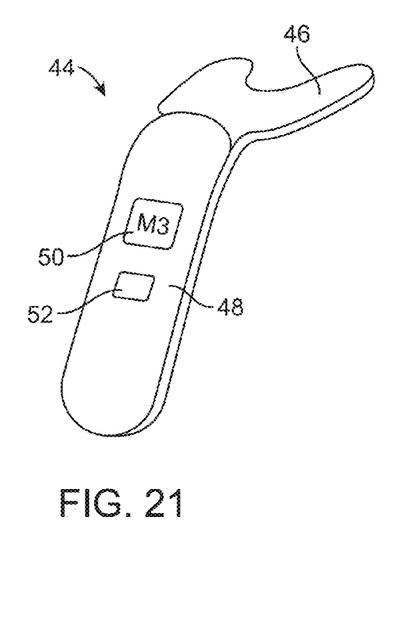
FIG. 21 illustrates a hand-held device having an integrated pressure-sensitive bite plate which may be utilized for performing the methods of the present invention.
Figure 22:
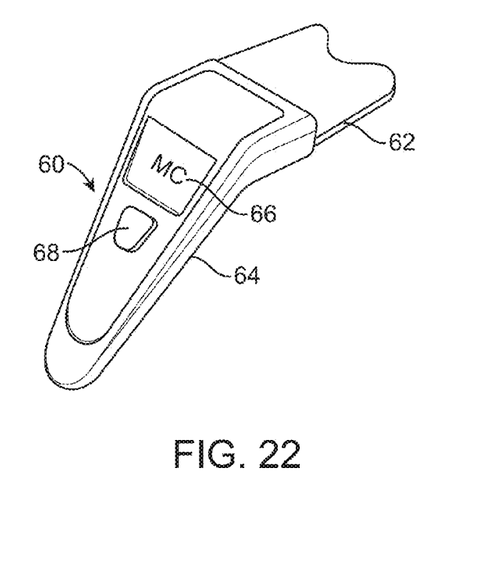
FIG. 22 illustrates a hand-held device having an integrated oral camera which may be utilized for performing the methods of the present invention.

Other integrated devices intended for performing the methods of the present invention are illustrated in FIGS. 21 and 22. In FIG. 21, an integrated device 44 having a pressure-sensitive plate 46 is shown. A handle 48 can include the processor (not shown), a display screen, and a button or other user interface to operate the system. As shown in FIG. 22, an integrated device 60 having an on board intra-oral camera 62 is shown. Handle 64 will include the processor (not shown) as well as a display 66, button or other user interface 68, and the like.

Figure 23:
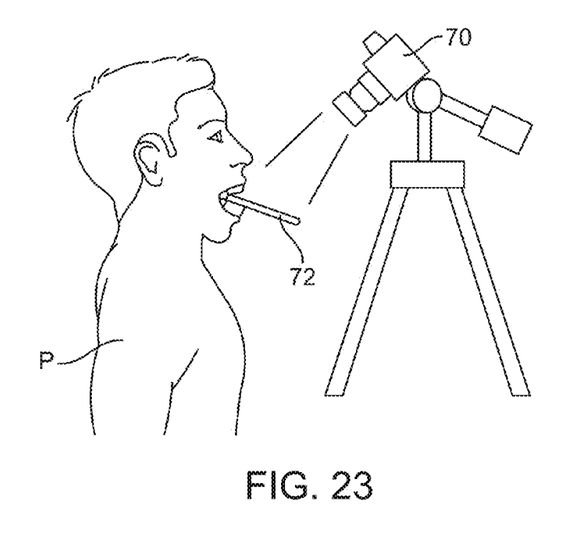
FIG. 23 illustrates use of a conventional camera for obtaining an image of the patient's dental arch using a mirror placed in the patient's oral cavity.

As shown in FIG. 23, a still further method for acquiring an image of the patient's dental arch is shown. A conventional electronic camera 70 can take an image of the arch using a mirror 72 which reflects an image of the upper dentition to the camera. The image can be sent from the camera 70 to the processor, either wirelessly or via a plug in cable, and the processor used to scale the image.

What is claimed is:

1. A method for selecting an oral appliance from an inventory of oral appliances, said method comprising:
   providing a wax bite plate with a size registration symbol;
   taking an image of a patient's teeth on the wax bit plate so that the wax bite plate has images of both the size registration symbol and the patient's teeth;
   scanning, by a mobile device, the wax bite plate to produce a digital image of the size registration symbol and the patient's teeth;
   presenting, by the mobile device, the digital image of the wax bite plate on a display of the mobile device;
   overlaying, by the mobile device, a scaling symbol over the size registration symbol on the digital image of the wax bite plate on the display, wherein the mobile device determines the actual dimensions of tooth impressions on the digital image of the wax bite plate;
   marking on the digital image, presented by the mobile device, a location of the patient's incisors to obtain a length dimension measured axially from the molar locations to the incisor location;
   marking on the digital image, presented by the mobile device, at least two opposed locations on the patient's molars to obtain a width dimension measured laterally between said markers to obtain a width dimension;
   selecting, by the mobile device, an oral appliance size which will accommodate the patient's dental arch based on the width and length dimensions; and
   displaying, by the mobile device, the oral appliance size on the display.

2. The method as in claim 1, wherein the display comprises a touch screen and marking comprises touching the locations to be marked on the screen.

3. The method as in claim 1, wherein marking comprises aligning a cursor with a locations on the display.

4. The method as in claim 1, wherein the processor selects the oral appliance size from a look up table based on the provided dimensions.

5. The method as in claim 1, further comprising storing the image, marked locations, and the selected oral appliance size in a memory.

6. The method as in claim 5, wherein the memory is in a device which also comprises the display.

7. The method as in claim 5, wherein the memory is remote from a device which also comprises the display.

8. A device for selecting an oral appliance from an inventory of oral appliances, said system comprising:
   a wax bit plate with a size registration symbol; and
   a mobile device comprising:
      a display;
      a user interface; and
      a processor;
   the mobile device programmed to:
      (i) to receive from the camera a digital image of the wax bite plate having images of both a size registration symbol and a patient's dental arch to produce a digital image;
      (i) scan the wax bite plate to produce a digital image of the size registration symbol and a patient's teeth:
      (ii) present the digital image of the wax bite plate on the display;
      (iii) overlay a scaling symbol over the size registration symbol on the digital image of the wax bite plate on the display and determine the actual dimensions of tooth impressions on the digital image of the wax bite plate;
      (iv) mark on the digital image, via the user interface, a location of the patient's incisors to obtain a length dimension measured axially from the molar locations to the incisor location;
      (v) mark on the digital image, via the user interface, at least two opposed locations on the patient's molars to obtain a width dimension measured laterally between said markers to obtain a width dimension; and
      (vi) select an oral appliance size which will accommodate the patient's dental arch based on the width and length dimensions; and
      (vii) display the oral appliance size on the display.

9. The system as in claim 8, wherein the display and user interface comprise a touch screen.

10. The system as in claim 8, wherein the display, the user interface, the camera, and the processor are incorporated into a common housing.

* * * * *